United States Patent [19]

Bianchi et al.

[11] Patent Number: 5,196,512
[45] Date of Patent: Mar. 23, 1993

[54] SYNTHETIC PEPTIDES USEFUL AS UNIVERSAL CARRIERS FOR THE PREPARATION OF IMMUNOGENIC CONJUGATES AND THEIR USE IN THE DEVELOPMENT OF SYNTHETIC VACCINES

[75] Inventors: Elisabetta Bianchi; Antonello Pessi, both of Rome, Italy; Giampietro Corradin, Lausanne, Switzerland

[73] Assignee: Eniricerche S.p.A., Milan, Italy

[21] Appl. No.: 610,525

[22] Filed: Nov. 8, 1990

[30] Foreign Application Priority Data

Nov. 10, 1989 [IT] Italy .................................. 22355 A/89

[51] Int. Cl.⁵ ........................... C07K 7/08; C07K 7/10; C07K 17/00; A61K 39/385
[52] U.S. Cl. ................................. 530/326; 530/322; 530/324; 530/327; 530/403; 530/405; 424/88; 424/89; 424/92; 930/200; 930/210
[58] Field of Search ............... 530/322, 324, 326, 327, 530/403, 405; 424/88, 89, 92; 930/200, 210

[56] References Cited

U.S. PATENT DOCUMENTS 4,695,624 9/1987 Marburg et al. ..................... 530/395
5,023,077 6/1991 Gevas et al. ........................... 424/88

FOREIGN PATENT DOCUMENTS 0166410  1/1986  European Pat. Off.
0209643  1/1987  European Pat. Off.
0289110 11/1988  European Pat. Off.
0306912  3/1989  European Pat. Off.
0320034  6/1989  European Pat. Off.
86/00911  2/1986  PCT Int'l Appl.
86/05790 10/1986  PCT Int'l Appl.
2199038  6/1988  United Kingdom.

OTHER PUBLICATIONS

Covey et al. (1989) Am. J. Reprod. Immunol. 19:17-20.
Lise et al (1988) Biochem. Biophys. Res. Commun. 153:31-38.
Hoffman et al (1987) Science 237:639-642.
Herrington et al (1987) Nature 328:257-259.
Miller et al (1986) Science 234:1349-1356.
Young et al (1985) Science 228:958-962.
Anuradha et al (1989) Med. Sci. Res. 17:477-479.
Demotz et al (1989) J. Immunol. Methods 122:67-72.
Esposito et al (1989) Biopolymers 28:225-246.
Hollingdale et al (1987) Expt. Parasitol. 63 345-351.
Lise et al (1989) Peptide Res. 2(1):114-119.
Panina-Bordignon et al (1989) in *Cold Spring Harbor Symposia on Quantitative Biology* vol. LIV Cold Spring Harbor Laboratory Press pp. 445-451.
Panina-Bordiguon et al (1989) Eur. J. Immunol. 19:2237-42.
Zavala et al (1986) J. Immunol Methods 93:55-61.

(List continued on next page.)

Primary Examiner—Christine M. Nucker
Assistant Examiner—Kay K. Kim
Attorney, Agent, or Firm—Shea & Gould

[57] ABSTRACT

The synthetic peptide TT3, the amino acid sequence of which corresponds to the region 947-967 of the tetanus toxin is recognized by different human Th cell clones in association with a wide range of alleles of the human major histocompatibility complex (MHC). Said peptide contains at least two epitopes, of which one (953-967) is recognized by the DR5-restricted clones and the other (947-960) is recognized by all other DR and DP alleles restricted clones. The TT3 peptide and the peptide corresponding to the 947-960 epitope can be used as universal carriers in the preparation of immunogenic conjugates consisting of at least one of said peptides and a natural or synthetic hapten derived from a pathogenic agent of interest.

The immunogenic conjugates are particularly suitable for preparing synthetic vaccines able to provide a protective immunity against different pathogenic agents which is not genetically restricted or is only slightly genetically restricted.

1 Claim, 3 Drawing Sheets

U.S. PATENT DOCUMENTS

Zavala et al (1987) in *CRC Synthetic Vaccines* vol. II, Chapter 20 pp. 149–159.

Chemical Abstracts, vol. 111, 1989, p. 495, Abstract No. 113289e. Anuradha et al.

Chemical Abstracts, vol. 111, 1989, p. 588, Abstract No. 192695k. Lise et al.

Chemical Abstracts, vol. 110, 1989, pp. 304–305, Abstract No. 208016g. Esposito et al.

Chemical Abstracts, vol. 107, 1987, pp. 529–530, Abstract No. 173783p. Hollingdale et al.

Chemical Abstracts, vol. 106, 1987, p. 437, Abstract No. 16623y. Zavala et al.

Gibson et al, (1986) Proceedings of the National Acad. of Sci., vol. 83, pp. 5649–5653, "Predicted Conformations for the Immunodominant Region of the Circumsporozoite Protein of the Human Malaria Parasite *Plasmodium falciparum*".

Togna et al, (1986) Journal of Imm., vol. 137, pp. 2956–2960, No. 9, "Synthetic Plasmodium Falciparum Circumsporozoite Peptides Elicit Heterogenous L3T4+ T Cell Proliferative Responses in H-$2^b$ Mice[1]".

Akaji et al, Chem. Pharm. Bull. 37(6), 1989, pp. 1612–1615, "Studies on Peptides. CLXVII. Solid–Phase Syntheses and Immunological Properties of Fragment Peptides Related to Human Malaria Circumsporozoite Protein".

SYNTHETIC PEPTIDES USEFUL AS UNIVERSAL CARRIERS FOR THE PREPARATION OF IMMUNOGENIC CONJUGATES AND THEIR USE IN THE DEVELOPMENT OF SYNTHETIC VACCINES

This invention relates generally to immunogenic conjugates consisting of a universal peptide carrier covalently bound to a hapten derived from a pathogenic agent of interest and their use in the development of synthetic vaccines. In particular, the present invention relates to synthetic peptides having the amino acid sequence corresponding respectively to the amino acid residues 947-967 and 947-960 of the tetanus toxin useful as universal carriers in the preparation of immunogenic conjugates.

The invention also relates to the use of said immunogenic conjugates in the development of vaccines able to induce protective immunity against different pathogenic agents which is not genetically restricted or only slightly so.

The term "hapten" signifies a molecule able to bind to specific antibodies (antigenic) but not to induce antibody formation or to induce it to only a low antibody count (not immunogenic).

Specifically, haptens include peptide or polysaccharide molecules (thymoindependent antigens) isolated and purified from pathogenic agents or short peptides with a sequence corresponding to that of one or more B epitopes of a natural antigen obtained by chemical synthesis or via recombinant DNA.

The term "antigen" signifies a molecule able to induce the formation of specific antibodies (immunogenic) and to react with them (antigenic).

Natural antigens include microorganisms, cells and their soluble products.

Immunisation against infection caused by pathogenic agents (viruses, parasites and bacteria) is generally obtained by inoculating an individual with a vaccine containing a natural antigen or antigens (attenuated or killed microorganisms or their suitably treated products) which stimulates the production of antibodies able to neutralise the antigen itself. The use of said traditional vaccines has however numerous drawbacks deriving both from the limited availability of the natural antigenic material and from the danger of possible infection while handling said pathogenic material.

In addition, these vaccines require preparation and storage (low temperature) conditions which can constitute an enormous problem, especially in underdeveloped countries.

For all these reasons there is currently an increasing interest in the development of synthetic vaccines which contain not the whole pathogen or its immunogenic product but instead short peptide fragments which reproduce segments of the natural antigen, which are known as epitopes or determinants or antigenic sites.

The preparation of such a vaccine therefore requires the identification and the selection of the peptides to be used.

It is known that an immune response towards a foreign agent by an organism involves the cooperation of various types of cells, namely antigen-presenting cells (APC), B lymphocytes (antibody producers able to function as APCs), T-helper (or Th) lymphocytes and T-cytotoxic lymphocytes responsible for directly killing the cells infected by the pathogen.

The immunity can be humoral (mediated by the antibodies produced by the B cells) or can be cell-mediated.

Considering humoral immunity, the minimum requirement for initiating an effective immune response is that the B lymphocytes of an antigenic determinant recognise the foreign substance (B epitope) and that the T lymphocytes of a determinant, generally different from B, recognise the same substance (T epitope). Consequently an effective synthetic vaccine should contain at least two peptide sequences corresponding respectively to the B epitope and the T epitope.

While the identification of the B epitope or epitopes contained in a natural antigen is facilitated by the possibility of using natural anti-pathogenic antibodies as reactants, localizing the T epitopes presents very complicated problems.

In this respect, the first case involves direct interaction between the anti-pathogenic antibody and the antigen, whereas in the second case the activation of the T cell clone specific for an epitope of the antigen takes place only after this has been interiorized by an APC, processed by proteolysis or denaturation or both in short peptide fragments, and then re-exteriorized on the surface of the APC in association with a membrane molecule of the class II cell (for the T-helpers) encoded by a gene of the major histocompatibility complex (MHC). The Th lymphocyte receptor therefore recognises not the free antigen but the complex formed between its fragment and a part of the class II MHC molecule. These molecules are grouped in three families DR, DP and DQ for man (HLA) and IA and IE for the mouse, and are extremely polymorphous.

The polymorphism is due to a large number of alleles for each of the encoding genes for this molecule, this diversity allowing a large number of combinations in a chromosome (haplotype). It is therefore very difficult to find individuals not linked by family relationship who have an identical MHC.

The fact that only some of the peptides deriving from the antigen degradation are able to associate with a host-histocompatible antigen means that the gene set of the host, which encodes said antigens, restricts the number of peptides able to form a complex with them, this however being an essential condition for activation of the Th lymphocytes.

The term "genetic restriction" of the T epitopes is therefore used in the sense that said peptide fragments are restricted in their interaction with the T lymphocyte receptor by the proteins with which they are associated. This is the basis of the difficulty of identifying within a natural antigen the T epitope or epitopes with absent or minimum genetic restriction and suitable for the development of synthetic acellular vaccines with wide effectiveness, i.e. able to induce protective immunization against the pathogenic agent of interest in individuals with different MHC gene sets.

Up to the present time this difficulty has been very often overcome by using as the source of T epitopes a macromolecule, also known as a carrier, to which a natural or synthetic peptide or polysaccharide hapten derived from a pathogenic agent of interest is covalently bound.

Examples of carriers suitable for this purpose are the tetanus toxoid (TT), the diptheria toxoid (CRM), serum albumin and lamprey hemocyanin (KLH) in that they provide the resultant conjugate with minimum genetic restriction.

Conjugates comprising said carriers, also known as universal carriers, are able to function as T cell clone activators in individuals having very different gene sets.

In this respect, most of the animals used for in vivo tests and having different gene sets are able to activate an antibody response towards the conjugate antigen, i.e. they are responders. Even though this approach to the problem has proved effective, the use of macromolecular-hapten carrier conjugates in a process of immunization against a pathogenic agent still has numerous drawbacks due to the difficulty of standardizing their various preparation stages, the possible alteration of the antigenic properties of the hapten as a result of the conjugation reaction [J. P. Briand et al., J. Immunol. Methods, 78 (1985) 59-69], and finally the phenomenon known as "epitope suppression induced by the carrier" which causes suppression of anti-hapten antibody production in an individual already immunized with only the carrier [H. Etliniger et al., (1988), J. Immunol. 140, 626].

This phenomenon is observed in those cases in which the carrier used is a protein to which the host has already been exposed, such as the tetanus toxoid used for anti-tetanus vaccination.

In addition, the use of short peptide sequences as immunogens, even if these comprise both a B epitope and a T epitope of the natural antigen, has generally led to an immune response which is genetically much more restricted, i.e. a reduction in the number of responder animals and/or individuals [see for example A. R. Togna et al., J. Immunol., 137 (1986) 2956-2960; G. Del Giudice et al., J. Immunol. 137, (1986), 2962-2955; G. Del Giudice et al., Immunology 63, (1988) 187-191].

In conclusion, the immunogenicity of a determined epitope depends on three factors, namely the generation of the appropriate fragment, the presence of an MHC molecule which binds this fragment, and the presence of T cells able to recognise the complex formed. The absence of one of these factors can result in lack of immune response. Most of the experiments conducted on mice indicate that the absence of an immune response is due mainly to the lack of an appropriate MHC molecule. In this respect, said molecules are highly polymorphous and it has been shown that a certain peptide can bind only to one or, at most, to few alleles, but never to all (Babbit et al., (1985), Nature 317, 359; Burns et al., (1987), Science 235, 1353). There are also cases in which there is no immune response because the antigen is not appropriately processed.

It has now been surprisingly found that fragments of the tetanus toxin corresponding to the amino acid residues 947-967, originally defined as the DR5-restricted epitope, and 947-960 are recognised by the T cell clones isolated from different donors immunized with the tetanus toxoid in association with a large number of class II molecules. Consequently said fragments, which completely satisfy the requirements of immunogenicity, appear to be epitopes universally immunogenic in man.

Thus the present invention firstly provides synthetic peptides having an amino acid sequence corresponding to the amino acid residues 947-967 and 947-960 of the tetanus toxin, which are useful as universal carriers in the preparation of immunogenic conjugates.

The present invention further provides immunogenic conjugates consisting of a universal peptide carrier covalently bound to a natural or synthetic peptide or polysaccharide hapten derived from a pathogenic agent of interest, in which said peptide carrier has its amino acid sequence corresponding to the amino acid residues 947-967 or 947-960 of the tetanus toxin.

The present invention also relates to the use of said immunogenic conjugates in the preparation of widely effective synthetic vaccines protective against pathogenic agents of interest. The present invention further provides synthetic vaccines for immunizing individuals with different MHC gene sets against infections caused by a pathogenic agent, characterised by containing an immunologically effective quantity of said immunogenic conjugates.

Further objects of the present invention will be apparent from reading the text and the following examples.

Specifically, the synthetic peptides 947-967 and 947-960 according to the present invention can be represented respectively by the following amino acid sequences:

-Phe-Asn-Asn-Phe-Thr-Val-Ser-Phe-Trp-Leu-Arg-Val-Pro-Lys-Val-Ser-Ala-Ser-His-Leu-Glu (Sequence No. 1);

-Phe-Asn-Asn-Phe-Thr-Val-Ser-Phe-Trp-Leu-Arg-Val-Pro-Lys (Sequence No. 6).

According to the present invention the synthesis of said peptides can be conducted in the solid phase or in the homogeneous phase, operating in accordance with one of the known general methods. The synthesis is preferably conducted in the solid phase using a commercial polyacrylamide resin, 4-hydroxymethylphenoxyacetic acid as the reversible peptide-resin handle and the fluorenylmethoxycarbonyl group (Fmoc) as the N-terminal protector group for the amino acid residues in accordance with the strategy described in Example 1.

The reactive functional side-chain groups of the amino acid residues are protected using protector groups chosen from those generally used in peptide synthetic.

Preferably, the trifluoroacetyl group (TFA) is used for the lysine (Lys), tert-butyl ether (Bu$^t$) for the serine (Ser) and threonine (Thr), the t-butyloxycarbonyl group (Boc) for the histidine, tert-butyl ester (OBu$^t$) for the glutamic acid (Glu) and the 4-methoxy-2,3,6-trimethylbenzenesulphonyl group (Mtr) for the arginine (Arg).

The suitably protected amino acids are condensed individually as symmetrical anhydrides or esters of pentafluorophenol and/or p-nitrophenol and/or 3,4-dihydro-3-hydroxy-4-oxobenzotriazine.

The peptides are removed from the resin, according to the present invention, by using an aqueous solution of trifluoroacetic acid at ambient temperature (20°-25° C.) for the time necessary to simultaneously remove the protector groups of t-butyl type but not the TFA or Mtr.

This strategy enables peptides to be obtained in which the only free amino group available for subsequent conjugation with a hapten is the N-terminal group (Phe). The peptides synthesized in this manner can be purified by gel filtration chromatography using normal methods.

In accordance with the present invention the capacity of the peptide 947-967, hereinafter call TT3, to stimulate the profilation of human T cell clones in the presence of APCs with different sets of class II HLA molecules was tested. It was found that peripheral blood mononucleate cells (PBMC) isolated from different individuals (typized HLAs) immunized with the tetanus toxin responded in vitro to the peptide TT3. These results suggested that said peptide could associate with many different class II MHC molecules. To confirm the results obtained, a proliferation trial was conducted using the same PBMC cells but in the absence of the peptide.

The absence of cell growth confirmed that the peptide was recognized in association with numerous alleles of class II molecules.

To determine the T cell clone isotype, i.e. which of the three MHC class II molecules, DR, DP or DQ, was used as the restriction element, proliferation trials were carried out using anti-DR, anti-DP and anti-DQ monoclonal antibodies (Mabs).

The proliferation reaction was effected in the presence of autologous EBV-B cells and the peptide TT3.

In this manner it was found that both the anti-DR and the anti-DP Mabs strongly inhibited proliferation of said clones. This indicated that the DP and DR molecules were the restriction elements for the T cell clones specific for TT3. Said peptide was recognized in association with different DR molecules (5, 6, 7 and 9) and DP molecules (2 and 4). Consequently the peptide TT3 is universally immunogenic. According to the present invention, to determine whether the T cell clones restricted by the different DR and DP molecules recognized different determinants on the peptide TT3, proliferation trials were conducted using fragments of it without an N-terminal or C-terminal portion. The results obtained show clearly that TT3 contains at least two epitopes, one of which (953-967) is recognized by the DR-restricted T cell clones, and the other (947-960) by the T cell clones restricted by all the other DR and DP alleles.

Consequently the peptide corresponding to the amino acid sequence 947-960 can also be used as a universal carrier. Identification of the peptides according to the present invention is of fundamental importance for the development of synthetic vaccines.

In particular, the peptides according to the present invention are suitable as universal carriers for the preparation of peptide-hapten immunogenic conjugates.

In this respect they combine within themselves the advantages of the entire tetanus toxoid sequence, i.e. the capacity to induce the formation of anti-hapten antibodies in most vaccinated individuals, with the advantages relating to their small size (no epitope suppression and more effective control of the conjugation reactions with the hapten).

Examples of haptens which can be bound to said peptide carriers for the preparation of immunogenic conjugates according to the present invention are: peptides or polysaccharides derived from different pathogenic agents such as meningocci, pneumococci, Haemophilus influenzae, β-hemolytic streptococci and Escherichia coli.

Haptens suitable for the purposes of the present invention also include those synthetic peptides having the sequence corresponding to that of one or more B epitopes of a natural antigen.

The conjugation between a peptide carrier according to the present invention and a hapten can be effected using one of the conventional methods employed generally in this particular sector of the art.

Specifically, the conjugation can be conducted using glutaraldehyde as binding agent, as reported for example by Avremas and Ternyck (Immunochemistry 6, 53, 1969).

According to one embodiment of the present invention the peptide TT3 was used as universal carrier to improve the immunogenicity of synthetic peptides having an amino acid sequence corresponding to that of the immunodominant B epitope of the circumsporoite protein (CSP) of Plasmodium falciparum, which is the etiologic agent of the most serious form of malaria (malignant tertian malaria) in man.

Said synthetic peptides, having the amino acid sequence H-(Asn-Ala-Asn-Pro)$_n$-OH (NANP)$_n$ where n is between 3 and 40, were in fact not able to induce an anti-CSP antibody response in CBA and DBA/2 mice (non-responder mice) [G. Del Giudice et al., J. Immunol., 137, 2952-2965 (1986)].

In this respect it was shown that (NANP)$_n$ contained within its sequence one or more T epitopes all genetically restricted by the I-A$^b$ allele of the H-2 murine histocompatibility complex present only in C57 BL/6 mice.

Said peptides were prepared as described in U.S. patent application Ser. No. 850,135 by polymerizing the activated monomer HCl.H-Asn-Ala-Asn-Pro-OPCP in the presence of triethylamine as basic initiator.

In accordance with the present invention the peptide carrier-(NANP)$_n$ conjugates were prepared by reacting the aldehyde groups of glutaraldehyde with the terminal amino group of the asparagine (Asn) of the (NANP)$_n$ and with the terminal amino group of the carrier.

The conjugation reaction was implemented in two stages. In the first stage the (NANP)$_n$ was left to react in a phosphate buffer (pH 7.4) with an excess of glutaraldehyde (OHCCH$_2$CH$_2$CH$_2$CHO) under neutrality conditions to give rise to the formation, by aldolic autocondensation, of the polymer with aldehyde functions:

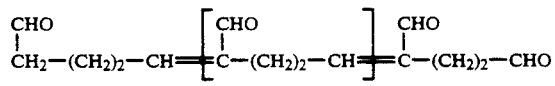

which seems to be the effective conjugation agent.

On termination of the conjugation reaction, the resultant product (NANP)$_n$-glutaraldehyde was purified from the unreacted glutaraldehyde by gel filtration.

In the second stage the (NANP)$_n$-glutaraldehyde conjugate was reacted in a phosphate buffer (pH 7.4) or in dimethylsulphoxide (DMSO) with a molar excess of the peptide carrier (between 2.5 and 25) with respect to the (NANP)$_n$-glutaraldehyde conjugate, so utilizing the presence of the still free aldehyde groups on the glutaraldehyde conjugated with the (NANP)$_n$ for attacking the terminal amino group of the carrier.

The reaction was conducted at ambient temperature (20°-25° C.) while stirring for 3 days, to obtain a yellowish solution.

A reducing substance can be added to said solution, such as NaBH$_4$ which, by reducing the bonds (Schiff's bases) between the amino group of the peptides and the aldehyde groups of the glutaraldehyde stabilizes the bonds present in the conjugate.

Preferably according to the present invention the NaBH$_4$ is used to give a further margin of safety in the stability of the bond between the two peptides.

The reduction reaction was conducted at ambient temperature for about two hours, on termination of which the formed precipitate was solubilized by adjusting the pH to an acid value.

The solution obtained was purified by gel filtration, eluting with 0.1M acetic acid to separate the formed conjugate from the excess peptide carrier.

One of the conventional methods was then used to release the protector groups of the amino functions in the side chains of the peptide carrier amino acid residues.

According to the present invention the protector group 4-methoxy-2,3,6-trimethylbenzenesulphonyl of the arginine of the TT3 peptide was removed by treating the conjugate with a trifluoro-acetic acid/phenol (95/5 v/w) solution, the trifluoroacetyl group of the lysine of the TT3 peptide being released by treatment with a basic aqueous solution.

The conjugates were then purified by lyophilization and chromatography.

According to the present invention the immunogenicity of said conjugates was verified by stimulating the in vitro proliferation of human T lymphocytes specific for the peptide carrier in the presence of autologous B cell lines as APCs.

In addition a determination was also made of the capacity of said conjugates to induce the production of anti-(NANP)$_n$ antibodies in mice who were non-responders to (NANP)$_n$.

The proliferation results showed both that the long (NANP)$_n$ sequence did not influence the capacity of the peptide carrier to function as a T epitope and that the conjugation reaction had not altered the structure of said T epitope.

In vivo immunization data (mice) also showed the absence of a genetic restriction and of an epitope suppression of the carrier. In fact, the mice who were non-responders to (NANP)$_n$ were able to produce a high concentration of anti-(NANP)$_n$ antibodies.

As stated heretofore, said peptide carriers are recognized within the ambit of the human restriction element DR and DP, and as there is considerable superimposing between the restriction elements of the human histocompatibility complex (HLA) and the murine (H-2), the experiments conducted on the mouse can be considered valid and the results can be extrapolated for man.

In conclusion the synthetic peptides according to the present invention are particularly suitable as universal carriers for the preparation of peptide carrier-hapten immunogenic conjugates able to induce protective immunity against different pathogenic agents which is not genetically restricted or with only slight genetic restriction.

Said conjugates can be administered to man in a single dose or in successive doses in the form of pharmaceutical compositions (vaccines) which contain them in a form and in a quantity suitable for inducing a protective immune response.

The preferred forms are pharmaceutical compositions prepared as suspensions or solutions containing the conjugate, which are easily administered by injection.

If desired, an adjuvant can be added to said compositions to improve their immune response.

The following experimental examples illustrate but do not limit the invention.

EXAMPLE 1

Synthesis of the peptide TT3

Figure 1:
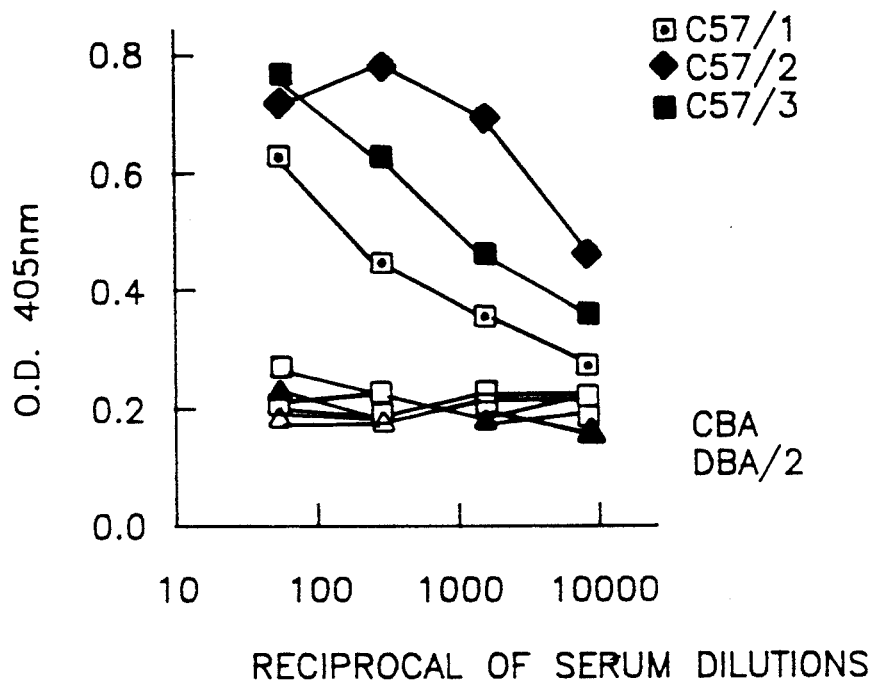
FIGS. 1, 2 and 3 show the production of anti-TT3 antibodies in mice after immunization with TT3 in combination with CFA (FIG. 1), in combination with CFA after boosting (FIG. 2), and in combination with IFA (FIG. 3).

The peptide TT3 was synthesized in the solid phase with a Biolynx 4070 automatic flow synthesizer (Pharmacia, LKB) using a commercial polyacrylamide resin (Ultrasyn, Pharmacia, LKB) functionalized with norleucine as internal reference amino acid, and 4-hydroxymethyl-phenoxyacetic acid as reversible peptide-resin handle.

1 g of said resin with a functionalization of 0.1 milliequivalents per gram was placed in a glass column (10×1 cm, Omnifit) and swollen by pumping N,N-dimethylformamide (DMF) for 30 minutes at a flow rate of 4 ml/min. This flow rate was kept constant in all subsequent operations.

The first amino acid residue (Glu) protected at the alpha-amino group by the protector group fluorenylmethoxycarbonyl (Fmoc) and at the carboxyl in the gamma position by the tert-butyl ester group, was esterified at the resin by the amino acid symmetric anhydride reaction in the presence of the catalyst 4-dimethylamino pyridine (DMAP).

In practice, 0.256 g (0.3 mmoles) of (Fmoc-Glu)-[OBu$^t$]$_2$O were dissolved in 2 ml of DMF in the presence of 0.004 g (0.03 mmoles) of DMAP and 0.033 ml (0.3 mmoles) of N-methylmorpholine (NMM) and reacted with the resin for 30 minutes.

On termination of the esterification reaction, the resin was washed with DMF (pumped through the column for 10 minutes), then with a solution of piperidine in DMF (2:8, v/v) for 10 minutes and finally with DMF for 10 minutes.

The solution (2 ml) of DMF containing the next amino acid activated at the carboxyl group and protected at the alpha amino group and possibly at the reactive side chain group was then added to the mixture to give rise to the acylation reaction at the free —NH$_2$ groups of the growing peptide chain.

The side chain functions of the amino acids were protected respectively with t-butylester (OBu$^t$) for the glutamic acid, t-butylether (Bu$^t$) for the serine and threonine, 4-methoxy-2,3,6-trimethylbenzenesulphonyl (Mtr) for the arginine, t-butyloxycarbonyl (Boc) for the histidine and trifluoroacetyl (TFA) for the lysine.

The stated washing and Fmoc removal operations were carried out between one acylation reaction and the next. The acylation reaction was conducted at ambient temperature for 60 minutes (recirculating system).

All the amino acid residues with the exception of the arginine (Arg), the serine (Ser) and the threonine (Thr) were introduced using, as activ form, the corresponding pentafluorophenol (Pfp) esters (0.3 mmoles in 2 ml of DMF) in the presence of 0.041 g (0.3 mmoles) of 1-hydroxybenzotriazole (HOBt).

For Arg, Ser and Thr the esters of 3,4-dihydro-3-hydroxy-4-oxobenzotriazine (DhBt) (0.3 mmoles in 2 ml of DMF) were used. The esters were dissolved in DMF immediately before adding the deprotected resin, by an automatic procedure of the synthesizer. For each acylation reaction, the completion of the reaction was checked by the ninhydrin test [E. Kaiser et al., Anal. Biochem., 34 (198), 595] and the trinitrobenzosulphonic acid test [W. S. Hancock et al., Anal. biochem., 71, (1976), 261].

Samples taken after 30 minutes of reaction gave positive results (absence of free amino groups on the resin).

On amino acid analysis, the resin-peptide gave the following results:

Phe, 2.70 (3); Asn, 1.82 (2); Thr, 0.80 (1); Ser, 2.70 (3); Val, 2.57 (3); Trp, n.d. (1); Arg, 0.89 (1); Lys, 1.10 (1); Ala, 1.00 (1); His, 0.94 (1); Leu, 2.79 (3); Glu, 1.21 (1).

The theoretical values are shown in parentheses.

A part of the peptide TT3 was preserved in the resin for possible synthesis of peptides linked to TT3, whereas the remainder was cleaved by treatment at ambient temperature for 2 hours with the trifluoroacetic acid solution (TFA/$H_2O$=90/1, v/w).

Said solution removes the t-butylester, t-butylether and Boc protection groups but not the trifluoroacetyl and 4-methoxy-2,3,6-trimethylbenzenesulphonyl groups.

This strategy enabled the peptide to be obtained in which the only amino group useful for its conjugation with a hapten is the terminal phenylalanine (Phe) group. (The reactivity of the histidine imidazole ring towards the glutaraldehyde is much less). The TT3 peptide obtained was then purified by gel filtration chromatography.

The gel chromatography was conducted with an 85×2.6 cm column filled with Sephadex G-15, using a 0.1M acetic acid solution as eluent.

The amino acid analysis of the purified peptide gave the following results:

Phe, 2.69 (3); Asn, 1.90 (2); Thr, 0.89 (1); Ser, 2.60 (3); Val, 2.88 (3); Trp, n.d. (1); Arg, 0.88 (1); Lys, 1.05 (1); Ala, 1.00 (1); His, 0.97 (1); Leu, 2.75 (3); Glu, 1.10 (1).

EXAMPLE 2

Isolation of cell clones specific for the peptide TT3

Peripheral blood mononucleate cells (PBMC) isolated from different donors (HLA-typized) immunized with the tetanus toxoid were cultivated at a concentration of $7\times10^5$ in 200 μl of RPMI-HS culture medium [RPMI=RPMI1640 supplemented with 2 mM of glutamine, 1% of non-essential amino acids, 1% of sodium pyruvate, 50 μg/ml of kanamycin (Flow, Irvine, Scotland); HS=human serum (Swiss Red Cross, Bern)] in the presence (10 μM) or absence of the peptide TT3 in microplates comprising 96 flat bottom wells. After 6 days 30 units/ml of interleuchine-2 (IL-2) (Roche, Nutley, N.J.) were added to each well, and after a further 4 days the cultures were examined to check any cell proliferation. The positive cultures were then expanded in the same medium to which IL-2 had been added, and where tested for their capacity to recognize the peptide TT3. An aliquot of said T cells was transferred to wells of microplates comprising 96 round bottom wells, washed three times and resuspended in 200 μl of RPMI medium to which 10% of fetal calf serum (FCS) (Gibco, Paisley, Scotland) was added, in the presence (20 μM) or absence of the peptide TT3. As the activated human T cells express class II molecules, they are able to present the peptide to each other, to result in a visible agglutination after 6 hours at 37° C. The positive cultures were cloned by limiting dilution and the clones specific for the peptide were isolated and maintained under culture by periodic restimulation with irradiated allogenic PBMCs and phytohema glutinin (1%) (Gibco) as described by Lanzavecchia et al., (1988), Nature 334, 530. Only one specific clone was preserved from each positive culture. As shown in Table I, the clones specific for TT3 were easily isolated from all the donors independently of their DR type. The approximate frequency of cells specific for TT3 was between 1 in $3\times10^4$ and 1 in $3\times10^5$, and represented only 5% or less of all the T cells specific for the tetanus toxoid (TT).

TABLE I

| Donor (DR) (a) | Clones isolated | Independent restriction (b) |
|---|---|---|
| K (3, 5) | 9 | DR5 |
| G (5) | 3 | DR5 |
| 2G (1, 5) | 3 | DR5 |
| 1G (5) | 1 | DR5 |
| M (2, 9) | 4 | DR9 |
| S (7) | 4 | DR7 |
| 3G (3, 7) | 3 | DR7 |
| 4 (5, 6) | 4 | DR5 |
| 1B (4, 6) | 2 | DP2 |
| F (1, 8) | 4 | DP2 |
| A (6) | 8 | DP4 |
| 1P (2, 3) | 2 | DP? |
| 5 (3) | 2 | DR5JVM/DP4 |
| T (2) | 1 | — |
| 10 (1, 7) | 3 | |
| 7 (3) | 1 | |
| 9 (2, 4) | 1 | |
| 12 (3, 6) | 5 | | where:
(a): PBMCs from various DR typized donors were stimulated with the peptide, the specific clones being isolated and characterised for the restriction.
(b) indicates all the class II MHC alleles able to present the peptide to at least one T cell clone.

All the isolated clones proliferate in response both to the TT3 peptide and to the entire tetanus toxoid molecule presented by autologous APC cells, showing that they are effectively specific for TT.

These results indicate that TT3 is universally recognized after immunization with TT and is therefore able to associate with various class II molecules.

EXAMPLE 3

Characterization of the T cell clones specific for TT3

A) Test of cell proliferation in presence of APCs having different sets of class II HLA molecules The cultures were conducted in 200 μl of RPMI-FCS medium in flat bottom microplates.

$3\times10^4$ T cells were cultivated with $2\times10^4$ EBV-B cells as irradiated APCs (6000 R) or $10^5$ irradiated PBMCs (3500 R). The tetanus toxoid or the TT3 peptide was added to the cultures or used to pulsate the EBV-B cells. After 2 days at 37° C. in the presence of 5% $CO_2$ the cells were pulsated with 1 μCi $^3$H-thymidine (Amersham, spec. activity 5 Ci/mM). The radioactivity incorporated by the cells was determined after 16 hours by liquid scintillation. The results, expressed as the mean count per minute (cpm) of a double culture, showed that all the isolated clones proliferated in response to the specific peptide and to the whole tetanus toxoid molecule presented by the autologous APC cells, demonstrating that they were specific for TT.

These results also indicate that the TT3 peptide is universally recognized after immunization with TT and that this peptide must therefore be able to associate with a variety of class II molecules.

B) Determination of the restriction pattern of T cells

To determine the isotype of the class II molecules recognized by each T cell clone, proliferation tests were conducted using anti-DR, anti-DP and anti-DQ monoclonal antibodies, obtained respectively from the hybridoma ATCC L243 available from the American Type Culture Center, and SVPL3 (anti-DQ) and B7.21 (anti-DP) supplied by Dr. Hergen Spits and Roberto Accolla. In addition, to recognize the restriction alleles, each clone was tested for its capacity to proliferate in response to a group of HLA-homozygote EPBV-B cells either pulsated or not with the TT3 peptide.

The T cells were cultivated with autologous EBV-B cells in the presence of limiting concentrations of the TT3 and anti-DR monoclonal antibodies (L243, 1:4 of the culture supernatant) or anti-DQ or anti-DP monoclonal antibodies both as 1:1000 ascites. To identify the DR or DP restriction alleles a group of HLA-homozygote allogenic EBV-B cells were used as APCs. The cells were pulsated for 2 hours at 37° C. with the TT3 peptide or with the culture medium alone, washed 4 times and irradiated.

The results show that the clones specific for TT3 are either DR or DP restricted (Tables I and II). At least 4 different DRs (DR5,5JVM, 7 and 9) and 3 different DP alleles (DP2.1, DP2.2 and DP2.4) can present the TT3 peptide to the T cells.

These results indicate that the TT3 can bind various allotypical and isotypical forms of class II molecules.

TABLE II

| Recognition of TT3 in association with various DR and DP alleles | | | | | | | |
|---|---|---|---|---|---|---|---|
| | DP-restricted clones (cpm × $10^{-3}$) | | | DR-restricted clones (cpm × $10^{-3}$) | | | |
| APC (a) | AS1 | 1BS | FS2 | KS21 | SS2 | MS3 | 5S3 |
| QBL [DRw18 (3), DP2] | 4 | 128 | 72 | 0 | 0 | 0 | 0 |
| JVM [DRw11JVM85), DP2] | 0 | 46 | 25 | 0 | 0 | 0 | 99 |

TABLE II-continued

| Recognition of TT3 in association with various DR and DP alleles | | | | | | | |
|---|---|---|---|---|---|---|---|
| | DP-restricted clones (cpm × $10^{-3}$) | | | DR-restricted clones (cpm × $10^{-3}$) | | | |
| APC (a) | AS1 | 1BS | FS2 | KS21 | SS2 | MS3 | 5S3 |
| ATH [DRw11 (5), DP2] | 0 | 33 | 39 | 270 | 0 | 0 | 0 |
| HHK [DRw13 (6), DP4] | 72 | 1 | 1 | 0 | 0 | 0 | 0 |
| DKB (DR9, DP4) | 40 | 0 | 0 | 0 | 0 | 12 | 0 |
| PITOUT (DR7, DPn.t) | 61 | 0 | 0 | 0 | 128 | 0 | 0 | where:
(a) DR and DP typization of APCs

EXAMPLE 4

Identification of the minimum antigen sequence recognized by T cells

To check whether the T cell clones restricted by different molecules recognize the same region or different regions of the TT3 peptide in association with different class II molecules, proliferation tests were carried out using a series of deletion fragments of the TT3 peptide without the N-terminal or C-terminal region.

The proliferation results are given in Table III.

TABLE III

| Proliferative response of cell clones | | | | | | |
|---|---|---|---|---|---|---|
| T cell clones (b) | Peptides (a) | | | | | |
| APC (DR/DP) | A | B | C | D | E | F |
| 4S5; KRA (DR6) (c) | 8 (.08) | 0 | 0 | 0 | 0 | nd |
| 3GS1; PITOUT (DR7) | 9 (.01) | 0 | 0 | 0 | 0 | 67 (2) |
| MS3; DKB (DR9) | 29 (5) | 0 | 0 | 0 | 0 | 18 (10) |
| KS21; ATH (DR5) | nd | nd | nd | 309 (.04) | 0 | 0 |
| FS2; QBL (DP2) | 94 (.01) | 118 (.04) | 0 | 0 | 0 | 76 (.05) |
| AS11; AVL (DP4) | 181 (.01) | 86 (5) | 0 | 0 | 0 | 83 (.05) | where:
(a) = TT3 deletion peptides having the following amino acid sequences:
A (947-967): Phe—Asn—Asn—Phe—Thr—Val—Ser—Phe—Trp—Leu—Arg—Val—Pro—Lys—Val—Ser—Ala—Ser—His—Leu—Glu (Sequence No. 1);
B (949-967): Asn—Phe—Thr—Val—Ser—Phe—Trp—Leu—Arg—Val—Pro—Lys—Val—Ser—Ala—Ser—His—Leu—Glu (Sequence No. 2);
C (951-967): Thr—Val—Ser—Phe—Trp—Leu—Arg—Val—Pro—Lys—Val—Ser—Ala—Ser—His—Leu—Glu (Sequence No. 3);
D (953-967): Ser—Phe—Trp—Leu—Arg—Val—Pro—Lys—Val—Ser—Ala—Ser—His—Leu—Glu (Sequence No. 4);
E (955-967): Trp—Leu—Arg—Val—Pro—Lys—Val—Ser—Ala—Ser—His—Leu—Glu (Sequence No. 5);
F (947-960): Phe—Asn—Asn—Phe—Thr—Val—Ser—Phe—Trp—Leu—Arg—Val—Pro—Lys (Sequence No. 6);
(b) indicates the Dr or DP type of the APC cells;
(c) indicates the peptide concentration in micromoles required to induce 30% of maximum response.

The results show clearly that TT3 contains at least 2 epitopes, of which one (953-967) is recognised by the DR5-restricted clones and the other (947-960) is recognised by all other DR and DP allele restricted clones.

EXAMPLE 5

A) Production of anti-TT3 antibodies

Groups of three mice of each stock (C57BL/6, CBA and DBA/2) were immunized with 50 μg of the TT3 peptide in 50 μl of complete Freund's adjuvant (CFA) at the base of the tail. The C57BL/6 mice are natural responders to (NANP)$_{40}$ whereas the CBA and DBA/2 mice are non-responders.

After 15 days their serum was withdrawn and tested individually by means of an ELISA (FIG. 1).

Figure 2:
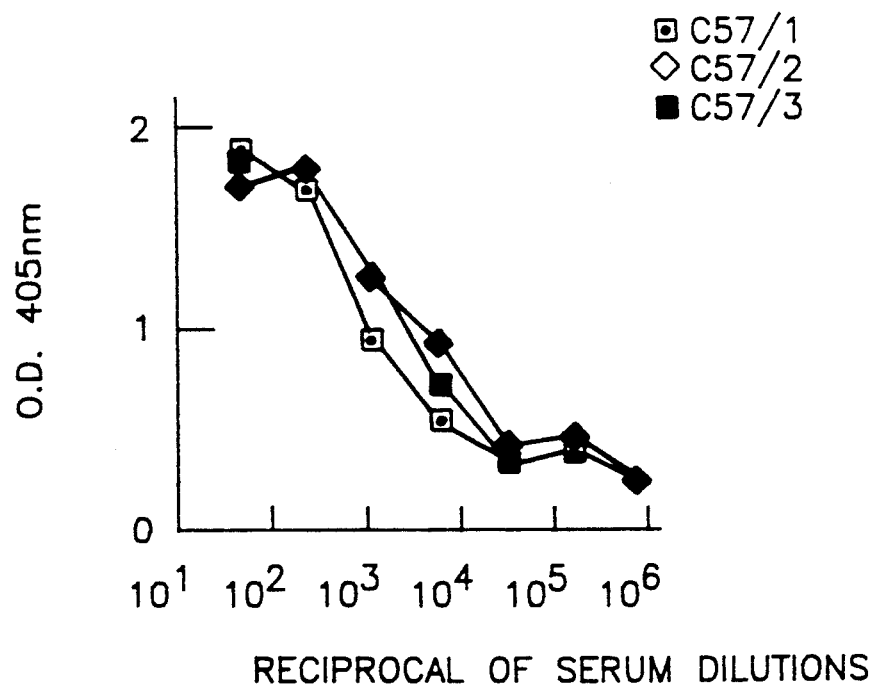

Only the C57BL/6 mice had produced anti-TT3 antibodies, the count of which increased after boasting (FIG. 2).

Figure 3:
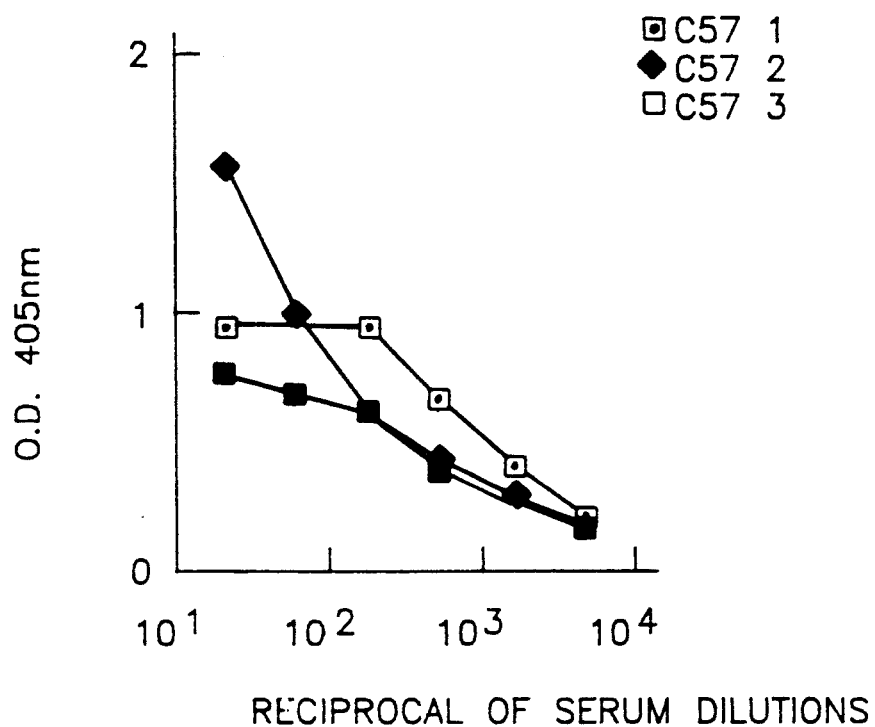

The use of CFA was not essential for obtaining a high antibody count in C57BL/6 mice immunized with the TT3 peptide. The same values were in fact obtained by the parallel immunization of a group of mice with 50 μg of TT3 in 50 μl of incomplete Freund's adjuvant (IFA) (FIG. 3).

B) Proliferative response to TT3 and its deletion fragments

Groups of three mice of each stock (C57BL/6, CBA and DBA/2) were immunized at the base of the tail with 50 μg of TT3 in 50 μl of CFA.

Figure 4:
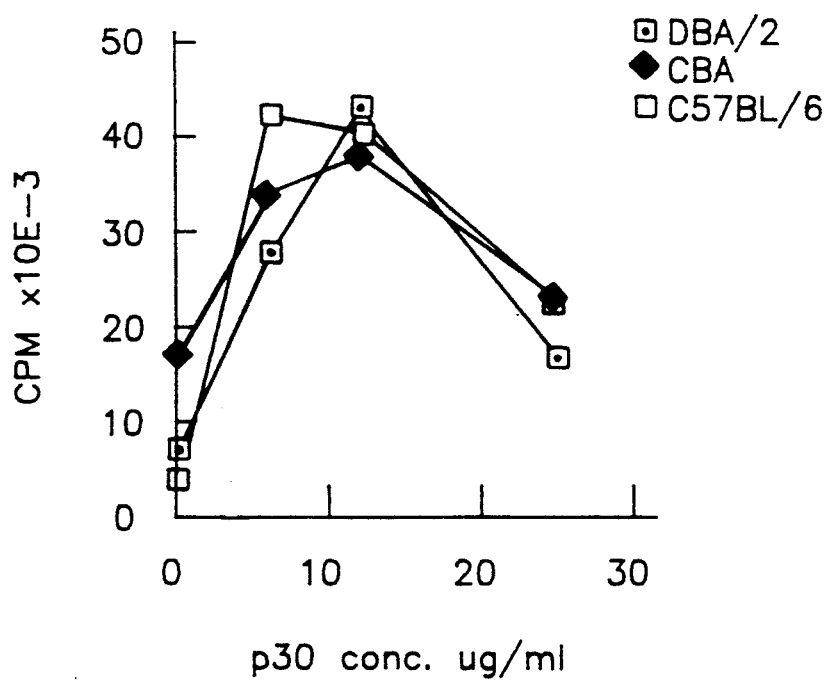
FIG. 4 shows the proliferative T-cell response of mice towards the TT3 peptide.

After 5 and 10 days the inguinal and paraaortic lymph nodes (LN) were removed and the suspensions of the lymph node cells of the individual mice were cultivated with different TT3 concentrations. All the tested mice showed good proliferative T cell response towards the TT3 peptide (FIG. 4).

The same test was carried out using the following peptides instead of TT3:
TT3 (947-967);
TT178C (949-967);
TT178B (951-967);
TT178A (953-967);
TT160 (955-967);
TT200 (947-960).

The results given in Table IV show that the different mice stocks recognise a similar peptide fragment.

TABLE IV

| Proliferative response to TT3 and its analogues | | | | |
|---|---|---|---|---|
| | | C57BL/6 | DBA/2 | CBA |
| TT3 | 947-967; | + | + | + |
| TT178C | 949-967; | + | + | + |
| TT178B | 951-967; | + | + | + |
| TT178A | 953-967; | + | − | − |
| TT160 | 955-967; | − | − | − |
| TT200 | 947-960 | − | − | − |

EXAMPLE 6

Synthesis of TT3-(NANP)n conjugates

A) Preparation of the TT3-(NANP)$_{40}$ conjugate 40 mg of (NANP)$_{40}$ were dissolved in 2.5 ml of phosphate buffer solution of pH 7.44 and then transferred to a 3 ml volume containing 52 μl (260 meq) of an aqueous 5% glutaraldehyde solution (FluKa), corresponding to a 100 times excess over the (NANP)$_{40}$.

The reaction mixture was kept under gentle stirring at ambient temperature overnight.

The solution was then chromatographed in an 85×2.5 cm column with Sephadex G-25 filling, eluting with 0.1M acetic acid. The fractions corresponding to the peak which elutes with the empty volume of the column corresponding to (NANP)$_{40}$ bound to the glutaraldehyde were then collected and lyophilized.

2.5 ml of dimethylsulphoxide (DMSO) containing the (NANP)$_{40}$-glutaraldehyde were added to a 3 ml reactor containing 88 mg (0.0375 mmoles) of TT3. The molar excess of TT3 over the (NANP)$_{40}$-glutaraldehyde was about 15 times.

The yellow solution obtained was left stirring for 3 days. On termination of the reaction 25 μg of NaBH$_4$ reducer were added. The resultant solution was stirred for a further two hours to obtain a suspended precipitate.

This precipitate was dissolved by adjusting the pH to about 4.0 by adding 1M acetic acid.

The solution was then purified by gel filtration on Sephadex G-25 eluting with 0.1M acetic acid to separate the resultant conjugate from the excess TT3.

The conjugation reaction yield, calculated by amino acid analysis, was 70%.

The TFA protector group for the lysine was removed by treatment with an aqueous solution of piperidine (1M) at ambient temperature (20°-25° C.) for 2 hours. The solution obtained was adjusted to pH 4 with dilute acetic acid and then again fed to the Sephadex G-25 column and eluted as stated heretofore. After lyophilization of the fraction corresponding to the conjugate, the protector group (Mtr) for the arginine of the TT3 peptide was removed by treatment with 5 ml of a TFA/phenol (95:5 w/v) solution for 5 hours.

The solution was evaporated to dryness under vacuum and the residue obtained was dissolved in 5 ml of H$_2$O, transferred to a 25 ml separator funnel and extracted twice with ethyl ether. The ether phase was re-extracted with water and the recovered aqueous phases were pooled and lyophilized.

The following conjugates were prepared in a like manner: TT3-Tyr(NANP)$_3$NA [0.0085 mmoles, 20 mg of TT3 plus 0.0085 mmoles (13.3 mg) of Tyr(NANP)-$_3$NA, yield 50%], and TT3-(NANP)$_{20}$ [88 mg of TT3 (0.0375 mmoles) plus 20 mg (0.0025 moles) of (NANP)$_{20}$, yield 73%].

EXAMPLE 7

Figure 5:
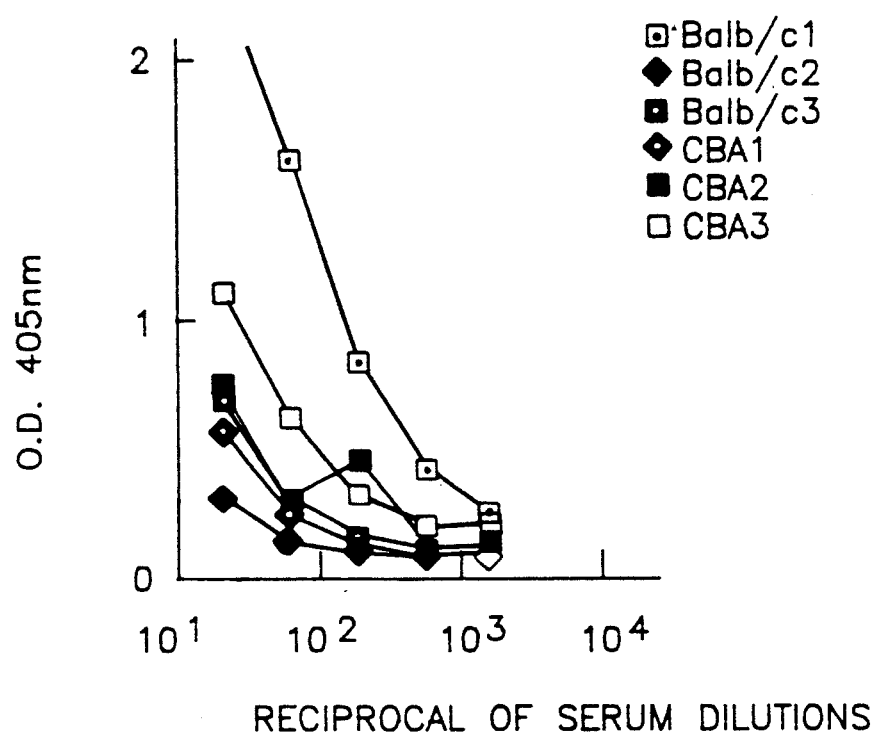
FIG. 5 shows the results of ELISAs conducted on dilutions of mouse serum after immunization with TT3-Tyr(NANP)$_3$NA conjugate.
Figure 6:
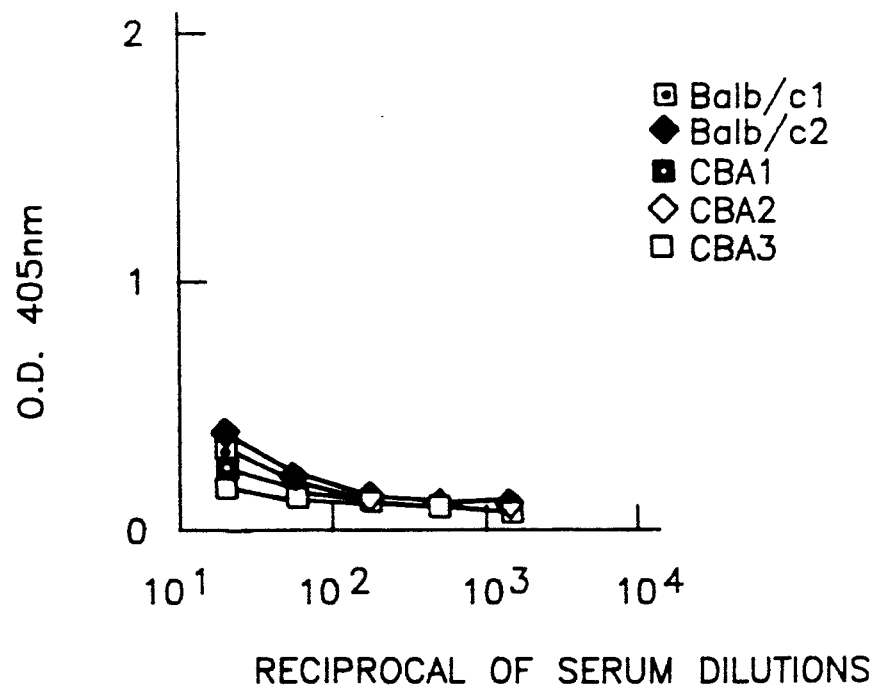
FIG. 6 shows the results of ELISAs conducted on different dilutions of mouse serum after immunization with Tyr (NANP)$_3$NA polymerized by glutaraldehyde.

Use of the TT3-Tyr(NANP)$_3$NA conjugate for the in vivo production of anti-NANP antibodies Groups of three CBA (H2-K) and Balb/c (H2-d) mice were immunized with 50 μg of the TT3-Tyr(-NANP)$_3$NA conjugate in 50 μl of CFA and after 2 weeks were again immunized with the same dose in IFA. The results of the ELISAs conducted on different dilutions of the serum withdrawn from each mouse are shown in FIG. 5. Control groups were immunized in parallel with Tyr(NANP)$_3$NA polymerized by glutaraldehyde (FIG. 6).

The results show that the TT3 peptide is recognised by various human DRs and by various murine IAs, in which it can be used as a B epitope carrier.

We claim:

1. An immunogenic conjugate comprised of a synthetic peptide carrier covalently bound to a hapten and able to induce a protective and genetically unrestricted antibody response against *Plasmodium falciparum*, said conjugate having the sequence:

synthetic peptide-(Asn-Ala-Asn-Pro)$_n$-OH wherein:

n is between 3 and 40 and the synthetic peptide is the carrier and is selected from Phe-Asn-Asn-Phe-Thr-Val-Ser-Phe-Trp-Leu-Arg-Val-Pro-Lys-Val-Ser-Ala-Ser-His-Leu-Glu (Sequence No. 1) or Phe-Asn-Asn-Phe-Thr-Val-Ser-Phe-Trp-Leu-Arg-Val-Pro-Lys (Sequence No. 6).

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:

( A ) LENGTH: 21 amino acid residues
( B ) TYPE: amino acid
( C ) STRANDEDNESS: single
( D ) TOPOLOGY: linear ( i i ) MOLECULE TYPE: peptide ( i i i ) HYPOTHETICAL: no ( v ) FRAGMENT TYPE: internal fragment ( x i ) SEQUENCE DESCRIPTION: SEQ ID NO:1:

| Phe | Asn | Asn | Phe | Thr | Val | Ser | Phe | Trp | Leu | Arg | Val | Pro | 12 |
| Lys | Val | Ser | Ala | Ser | His | Leu | Glu | | | | | | 8 |

( 2 ) INFORMATION FOR SEQ ID NO:2:

( i ) SEQUENCE CHARACTERISTICS:
( A ) LENGTH: 19 amino acid residues
( B ) TYPE: amino acid
( C ) STRANDEDNESS: single
( D ) TOPOLOGY: linear ( i i ) MOLECULE TYPE: peptide ( i i i ) HYPOTHETICAL: no ( v ) FRAGMENT TYPE: internal fragment ( x i ) SEQUENCE DESCRIPTION: SEQ ID NO:2:

| Asn | Phe | Thr | Val | Ser | Phe | Trp | Leu | Arg | Val | Pro | Lys | 12 |
| Val | Ser | Ala | Ser | His | Leu | Glu | | | | | | 7 |

( 2 ) INFORMATION FOR SEQ ID NO:3:

( i ) SEQUENCE CHARACTERISTICS:
( A ) LENGTH: 17 amino acid residues
( B ) TYPE: amino acid
( C ) STRANDEDNESS: single
( D ) TOPOLOGY: linear ( i i ) MOLECULE TYPE: peptide ( i i i ) HYPOTHETICAL: no ( v ) FRAGMENT TYPE: internal fragment ( x i ) SEQUENCE DESCRIPTION: SEQ ID NO:3:

| Thr | Val | Ser | Phe | Trp | Leu | Arg | Val | Pro | Lys | 10 |
| Val | Ser | Ala | Ser | His | Leu | Glu | | | | 7 |

( 2 ) INFORMATION FOR SEQ ID NO:4:

( i ) SEQUENCE CHARACTERISTICS:
( A ) LENGTH: 15 amino acid residues
( B ) TYPE: amino acid
( C ) STRANDEDNESS: single
( D ) TOPOLOGY: linear ( i i ) MOLECULE TYPE: peptide ( i i i ) HYPOTHETICAL: no ( v ) FRAGMENT TYPE: internal fragment ( x i ) SEQUENCE DESCRIPTION: SEQ ID NO:4:

Ser Phe Trp Leu Arg Val Pro Lys Val Ser Ala Ser His Leu Glu    15

( 2 ) INFORMATION FOR SEQ ID NO:5:

( i ) SEQUENCE CHARACTERISTICS:
( A ) LENGTH: 13 amino acid residues
( B ) TYPE: amino acid
( C ) STRANDEDNESS: single (D) TOPOLOGY: linear (ii) MOLECULE TYPE: peptide (iii) HYPOTHETICAL: no (v) FRAGMENT TYPE: internal fragment (xi) SEQUENCE DESCRIPTION: SEQ ID NO:5:

Trp Leu Arg Val Pro Lys Val Ser Ala Ser His Leu Glu    13

(2) INFORMATION FOR SEQ ID NO:6:

(i) SEQUENCE CHARACTERISTICS:
        (A) LENGTH: 14 amino acid residues
        (B) TYPE: amino acid
        (C) STRANDEDNESS: single
        (D) TOPOLOGY: linear (ii) MOLECULE TYPE: peptide (iii) HYPOTHETICAL: no (v) FRAGMENT TYPE: internal fragment (xi) SEQUENCE DESCRIPTION: SEQ ID NO:6:

Phe Asn Asn Phe Thr Val Ser Phe Trp Leu Arg Val Pro Lys    14

(2) INFORMATION FOR SEQ ID NO:7:

(i) SEQUENCE CHARACTERISTICS:
        (A) LENGTH: 4 amino acid residues
        (B) TYPE: amino acid
        (C) STRANDEDNESS: single
        (D) TOPOLOGY: linear (ii) MOLECULE TYPE: peptide (iii) HYPOTHETICAL: no (v) FRAGMENT TYPE: internal fragment (xi) SEQUENCE DESCRIPTION: SEQ ID NO:7:

Asn Ala Asn Pro    4